United States Patent [19]

Umezawa et al.

[11] 4,195,170
[45] Mar. 25, 1980

[54] 3',4'-EPISULFIDO KANAMYCIN B COMPOUNDS

[75] Inventors: Hamao Umezawa; Sumio Umezawa; Shigeo Seki; Shunzo Fukatsu, all of Tokyo; Shuntaro Yasuda, Yokohama, all of Japan

[73] Assignee: Zaidan Hojin Biseibutsu Kagaku Kenkyu Kai, Tokyo, Japan

[21] Appl. No.: 880,401

[22] Filed: Feb. 23, 1978

Related U.S. Application Data

[62] Division of Ser. No. 745,016, Nov. 26, 1976.

[30] Foreign Application Priority Data

Dec. 9, 1975 [JP] Japan ................................ 50/145930
Dec. 10, 1975 [JP] Japan ................................ 50/146345

[51] Int. Cl.$^2$ ............................................. C07H 15/22
[52] U.S. Cl. ................................... 536/10; 424/180; 536/17 R
[58] Field of Search ...................................... 536/10, 17

[56] References Cited

U.S. PATENT DOCUMENTS

| Re. 28,647 | 12/1975 | Umezawa et al. ...................... 536/10 |
| 4,060,682 | 11/1977 | Umezawa et al. ...................... 536/10 |

*Primary Examiner*—Johnnie R. Brown
*Attorney, Agent, or Firm*—Herbert W. Taylor, Jr.

[57] ABSTRACT

New routes are provided for the synthesis of 3',4'-dideoxykanamycin B which is effective in inhibiting kanamycin-resistant organisms from kanamycin B through new intermediate, of which a fundamental process comprises a new reaction of a 3',4'-epoxy derivative of amino- and hydroxyl-protected kanamycin B with a xanthate to form a corresponding 3',4'-dideoxy-3'-eno derivative followed by removal of the amino- and hydroxyl-protecting groups thereof and by hydrogenation of the resulting 3',4'-dideoxy-3'-eno-kanamycin B. A 3',4'-episulfide derivative corresponding to the 3',4'-epoxy derivative which is formed as second product in the reaction of 3',4'-epoxy derivative with xanthate is also used as intermediate for the preparation of 3',4'-dideoxykanamycin B.

3 Claims, No Drawings

3',4'-EPISULFIDO KANAMYCIN B COMPOUNDS

CROSS REFERENCE TO RELATED APPLICATION

This application is a division of our prior, co-pending application Ser. No. 745,016 filed Nov. 26, 1976.

BACKGROUND OF THE INVENTION

This invention relates to new routes for the synthesis of 3',4'-dideoxykanamycin B which is antibacterial against a variety of gram-positive and gram-negative bacteria and particularly effective in inhibiting kanamycin-resistant organisms such as kanamycin-resistant Staphylococci and kanamycin-resistant Escherichia coli.

DESCRIPTION OF THE PRIOR ART

3',4'-Dideoxykanamycin B having the structure:

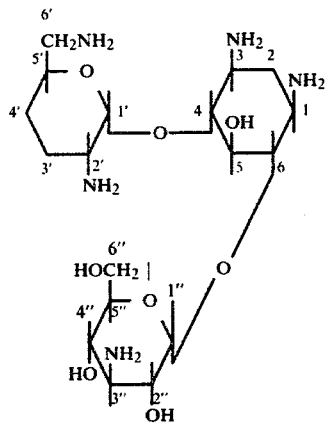

has hitherto been prepared by a method comprising protecting the five amino groups and all or a part of the hydroxyl groups other than 3'- and 4'-hydroxyl groups of kanamycin B by a conventional method, sulfonylating the 3'- and 4'-hydroxyl groups to afford a derivative having 3'- and 4'-disulfonic ester groups, removing the 3'- and 4'-disulfonic ester groups by known methods to give a 3',4'-unsaturated compound, reducing the 3',4'-unsaturated compound and removing the residual protecting groups. The known method requires nine steps from kanamycin B to 3',4'-dideoxykanamycin B (see British Patent Specification No. 1,349,302). Further, the method requires the use of sodium iodide and zinc powder in large amounts in the step for removing the 3'- and 4'-disulfonic ester groups, thus involving questions of iodine resources and of environmental pollution resulting from disposal of by-products. Therefore, the development of new, more advantageous method for synthesis of 3',4'-dideoxykanamycin B has eagerly been desired from the industrial point of view.

SUMMARY OF THE INVENTION

It is the primary object of this invention to provide some new routes for the synthetic preparation of 3',4'-dideoxykanamycin B which are advantageous over the prior art in that they do not use an alkali metal bromide or iodide and zinc powder, but use other reagents of less expenses. All the new processes originate from kanamycin B as in the prior art but pass through a new route of reaction.

According to a first aspect of this invention, therefore, there is provided a process for the preparation of 3',4'-dideoxykanamycin B or its acid addition salts which comprises (1) treating with a xanthate a 3',4'-epoxy derivative of an amino- and hydroxyl-protected kanamycin B of the formula:

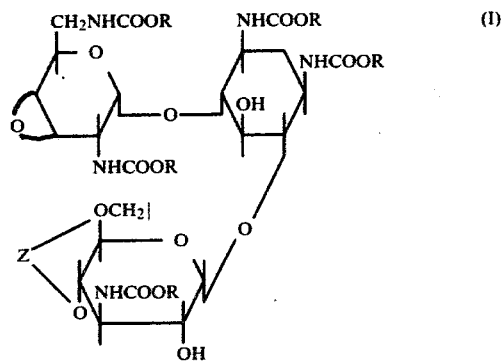

wherein R represents a hydrogen atom or an alkyl or aryl group, Z represents an alkylidene, arylidene, cyclohexylidene or tetrahydropyranylidene group and the 3',4'-epoxy group is in α- or β-position whereby to form a 3',4'-dideoxy-3'-eno-kanamycin B derivative of the formula:

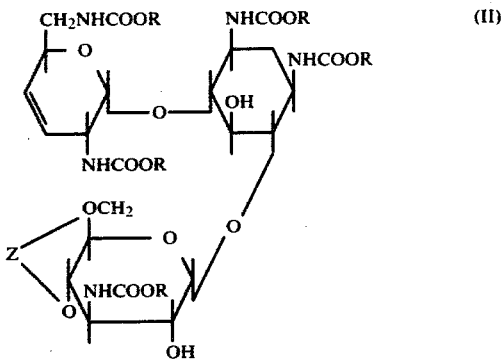

wherein R and Z have the same meaning as defined above together with a 3',4'-episulfido-kanamycin B derivative of the formula:

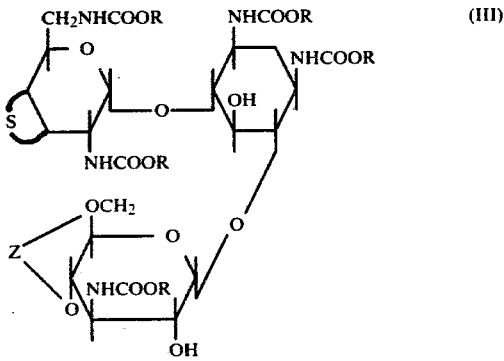

wherein R and Z have the same meaning as defined above and the 3',4'-episulfide group is in a α- or β-position;

(2) isolating the 3',4'-dideoxy-3'-eno-kanamycin B derivative from the reaction mixture;

(3) removing the amino-protecting groups —COOR and hydroxyl-protecting group Z of the 3',4'-dideoxy-3'-eno derivative thus isolated in a conventional manner to form 3',4'-dideoxy-3'-eno-kanamycin B of the formula:

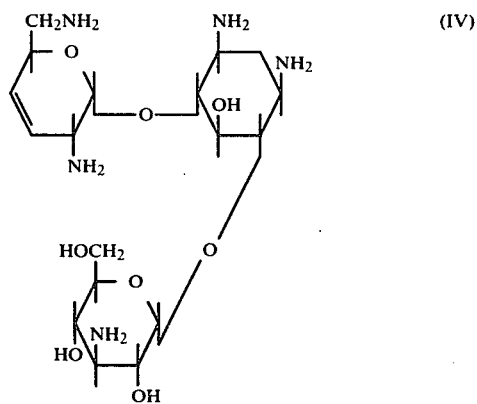

and (4) hydrogenating the compound thus formed in a conventional manner to form 3',4'-dideoxykanamycin B; and, if desired, converting the compound thus formed into an acid addition salt thereof.

The step (1) of the first aspect process of this invention, that is the treatment of a 3',4'-epoxy derivative of the formula (I) in either α- or β-form with a xanthate, may be effected in an organic solvent, preferably at a temperature of 50°~100° C. The organic solvent may preferably be a lower alkanol such as methanol and ethanol. The xanthate to be used for this treatment may be those of the formula R'OCSSMe where R' is a lower alkyl group, Me is an alkali metal such as sodium or potassium. Generally, this reaction gives a 3',4'-dideoxy-3'-eno derivative of the formula (II) as a first product in admixture with a 3',4'-episulfide derivative of the formula (III) as a second product after washing the reaction mixture with water, recovering the solvent by distillation and concentrating the residue to dryness.

The mechanism of reaction between the 3',4'-epoxy derivative of the formula (I) and the xanthate has not yet been made clear, but a presumable possibility is that the conversion of 3',4'-epoxy derivative into corresponding 3',4'-dideoxy-3'-eno derivative of the formula (II) proceeds via corresponding 3',4'-episulfide derivative of the formula (III).

The isolation of the first and second products of the step (1) from each other, i.e. the step (2) of the first aspect process, may be effected, preferably by chromatography, for example silica-gel thin layer chromatography in a usual manner, for example using a mixture (e.g. 1:1 by volume) of carbon tetrachloride and acetone as developer.

The step (3) of the first aspect process of this invention for the removal of the amino-protecting groups —COOR and hydroxyl-protecting group Z may be carried out in a usual manner. For example, the removal of the hydroxyl-protecting group Z may first be effected by a mild hydrolysis with a dilute hydrochloric acid or an aqueous acetic acid and then the amino-protecting groups may be removed by a hydrolysis with barium hydroxide or by hydrogenolysis in the presence of a palladium catalyst. The step (4) of the first aspect process, that is the hydrogenation step, may be carried out in a known manner. Thus, a catalytic reduction with hydrogen in the presence of a known hydrogenation catalyst comprising a platinum group metal such as platinum or palladium may preferably be applicable to the step (4). Raney nickel catalyst may also be used for this purpose.

The first aspect process of this invention is advantageous over the prior art process above-mentioned in that the formation of 3',4'-unsaturation can be achieved without relying on the reaction involving the use of an alkali bromide or iodide and zinc powder;

as the final intermediate compound which is to be converted to the desired product, 3',4'-dideoxykanamycin B, in the last step, 3',4'-dideoxy-3'-eno-kanamycin B, i.e. the compound of the formula (IV) free from any protecting group can be obtained;

in the last step, the catalytic hydrogenation can be achieved relatively easily with much less impurities derived from reagents used, so that the purification of the final product is required only to a less extent than in the prior art process wherein the step for removing amino- and hydroxyl-protecting groups is carried out after the step for the hydrogenation.

It will be appreciated, however, that the order of the steps (3) and (4) of the first aspect process of this invention can be reversed, if desired, to follow the known order adopted by the prior art process.

The final product, 3',4'-dideoxykanamycin B in free base form, may be converted, if desired, to an acid addition salt derived from an inorganic or organic acid. For example, sulfate of 3',4'-dideoxykanamycin B may be obtained by adding dilute sulfuric acid to an aqueous solution of the free base to adjust the pH value to 6.8, treating the solution with decoloring carbon, filtering the solution and freeze-drying the filtrate.

We have further found that the 3',4'-episulfide derivative of the formula (III) which is formed as second product in the step (1) of the first aspect process of this invention is also useful as intermediate for the preparation of 3',4'-dideoxykanamycin B. Our discovery in this respect is that there are two routes for converting the 3',4'-episulfide derivative of the formula (III) to a known useful intermediate for the preparation of 3',4'-dideoxykanamycin B; the first route is to treat the 3',4'-episulfide derivative with an acid to form 3',4'-dideoxy-3'-eno-kanamycin B of the formula (IV) and the second route is to treat the 3',4'-episulfide derivative with hydrazine or Raney nickel to form a 3',4'-dideoxy-3'-eno-kanamycin B derivative of the formula (II).

According to a second aspect process of this invention, therefore, we provide a process for the preparation of 3',4'-dideoxykanamycin B or its acid addition salts which comprises (1) treating with a xanthate a 3',4'-epoxy derivative of an amino- and hydroxyl-protected kanamycin B of the formula:

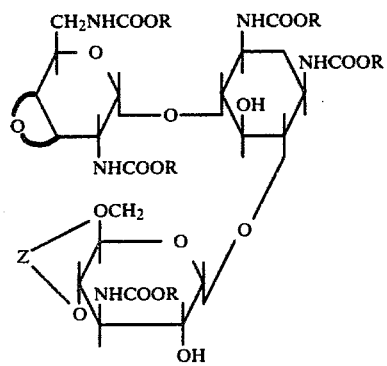

(I)

wherein R represents a hydrogen atom or an alkyl or aryl group, Z represents an alkylidene, arylidene, cyclohexylidene or tetrahydropyranylidene group and the 3′,4′-epoxy group is in α- or β-position whereby to form a 3′,4′-episulfidokanamycin B derivative of the formula:

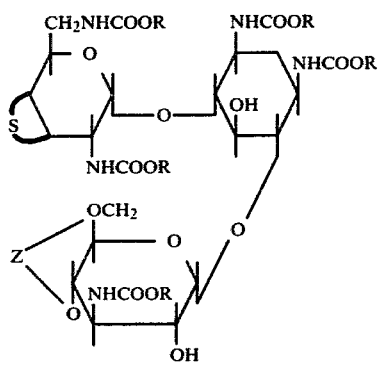

(III)

wherein R and Z have the same meaning as defined above and the 3′,4′-episulfide group is in α- or β-position together with a 3′,4′-dideoxy-3′-eno-kanamycin B derivative of the formula:

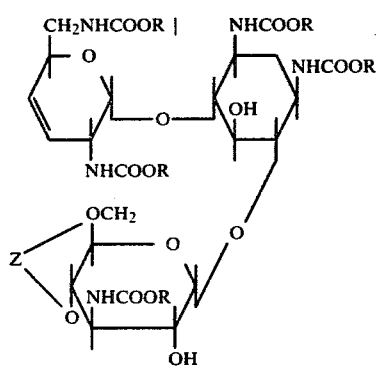

(II)

wherein R and Z have the same meaning as defined above;

(2) isolating the 3′,4′-episulfido-kanamycin B derivative from the reaction mixture;

(3) treating the 3′,4′-episulfide derivative thus isolated with an acid to form 3′,4′-dideoxy-3′-eno-kanamycin B of the formula:

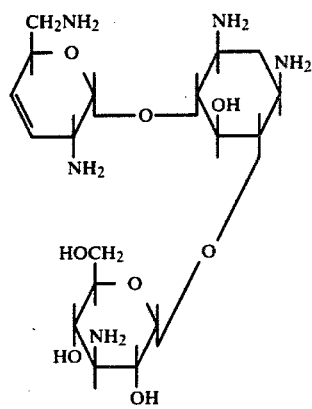

(IV)

and (4) hydrogenating the compound thus formed in a conventional manner to form 3′,4′-dideoxykanamycin B; and, if desired, converting the compound thus formed into an acid addition salt thereof.

The steps (1), (2) and (4) of the second aspect process of this invention correspond to the steps (1), (2) and (4) of the first aspect process as above-mentioned, respectively.

The step (3) of the second aspect process, i.e. the treatment of the 3′,4′-episulfide derivative of the formula (III) with an acid may preferably be carried out in a lower alkanol such as methanol and ethanol using a hydrohalogenic acid such as concentrated hydrochloric acid and hydrobromic acid. In general, however, a non-oxidizing mineral acid, for example sulfuric acid, may be used for this treatment. Preferably, the treatment may be carried out at a temperature of 0°~30° C.

According to a third aspect of this invention, there is provided a process for the preparation of 3′,4′-dideoxykanamycin B or its acid addition salts which comprises (1) treating with a xanthate a 3′,4′-epoxy derivative of an amino- and hydroxyl-protected kanamycin B of the formula:

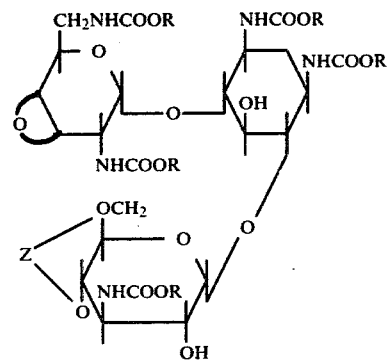

(I)

wherein R represents a hydrogen atom or an alkyl or aryl group and Z represents an alkylidene, arylidene, cyclohexylidene or tetrahydropyranylidene group whereby to form a 3′,4′-episulfido-kanamycin B derivative of the formula:

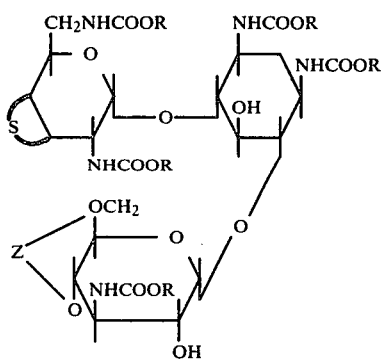

wherein R and Z have the same meaning as defined above and 3',4'-episulfide group is in α- or β-position together with a 3',4'-dideoxy-3'-eno-kanamycin B derivative of the formula:

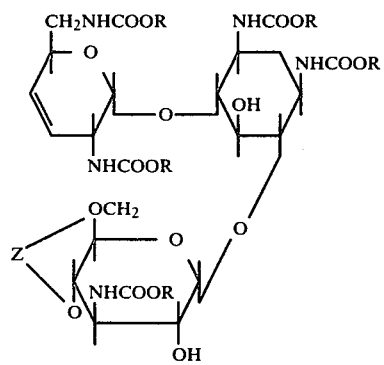

wherein R and Z have the same meaning as defined above;

(2) treating the reaction mixture from the step (1) with hydrazine or Raney nickel to convert the 3',4'-episulfide derivative of the formula (III) into a further amount of the 3',4'-dideoxy-3'-eno-kanamycin B derivative of the formula (II) above;

(3) removing amino-protecting groups —COOR and hydroxylprotecting group Z of the 3',4'-dideoxy-3'-eno derivative thus formed in a conventional manner to form 3',4'-dideoxy-3'-eno-kanamycin B of the formula:

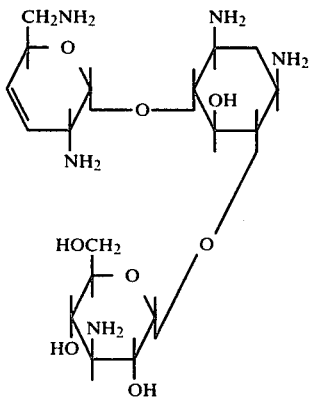

and (4) hydrogenating the compound thus formed in a conventional manner to form 3',4'-dideoxykanamycin B; and, if desired, converting the compound thus formed into an acid addition salt thereof.

The steps (1),(3) and (4) of the third aspect process of this invention correspond to the steps (1),(3) and (4) of the first aspect process as above-mentioned, respectively.

In the step (2) of the third aspect process the treatment with hydrazine may preferably be effected in a lower alkanol such as methanol and ethanol using hydrazine, particularly in the form of hydrate $NH_2NH_2 \cdot H_2O$, at room temperatures, usually 15°~25° C. The amount of hydrazine to be used may preferably be about 10~30 moles per mole of the compound of the formula (III). The treatment with Raney nickel, if adopted for the step (2), may preferably be carried out by dissolving the compound of the formula (III) in a lower alkanol, for example methanol, adding Raney nickel to the solution in an appropriate amount, for example threefold amount in respect of the amount of the compound of the formula (III) on the weight basis and maintaining the mixture under stirring at room temperatures, usually 15°~25° C. for 1~3 hours.

In the third aspect process of this invention, the step (2) is also applicable, if desired, to the 3',4'-episulfide derivative of the formula (III) which has been isolated from the 3',4'-dideoxy-3'-eno derivative of the formula (II), but it is usually advantageous to apply the step (2) directly to the reaction mixture from the step (1) containing both the compounds of the formulae (II) and (III) particularly in large scale operations.

We have further found that the 3',4'-dideoxy-3'-eno derivatives of the formula (IV) can be produced from the 3',4'-epoxy derivatives of the formula (I) through another route involving four steps with a high overall yield. This route comprises the steps of (1) treating a 3',4'-epoxy derivative of the formula:

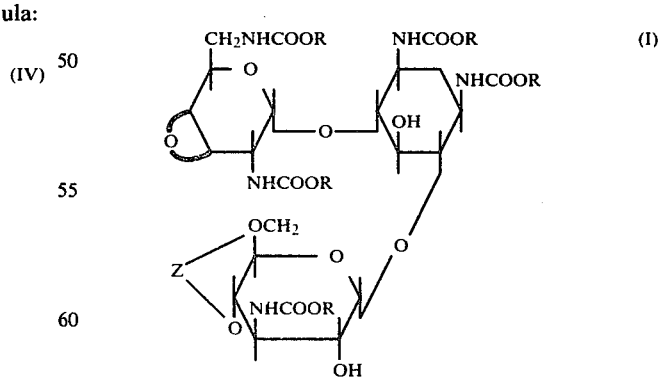

wherein R and Z have the same meaning as defined above with an acrylating agent, for example benzoyl chloride, in a conventional manner to acrylate the 2''-hydroxyl group, giving a compound of the formula:

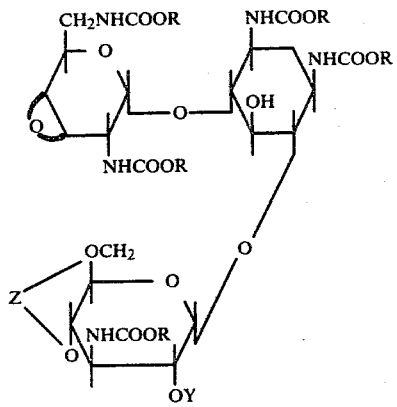

wherein R and Z have the same meaning as defined above and Y represents an acyl group;

(2) treating the compound of the formula (V) thus obtained with an alkali or alkaline earth metal iodide, for example sodium iodide, preferably in the presence of sodium acetate and glacial acetic acid, to give a compound of the formula:

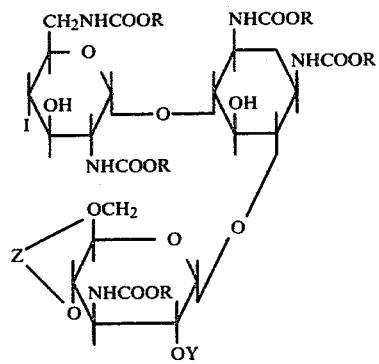

where R, Z and Y have the same meaning as defined above;

(3) subjecting the compound of the formula (VI) thus obtained to 3'-O-sulfonylation with a sulfonylating agent such as mesyl chloride, tosyl chloride and benzylsulfonyl chloride in a known manner, preferably in pyridine at a temperature below 10° C., to form the compound of the formula:

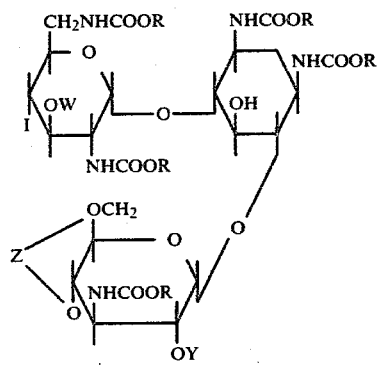

where R, Z and Y have the same meaning as defined above and W represents mesyl, tosyl or benzylsulfonyl group; (4) heating the reaction mixture from the step (3) above, preferably to a temperature of 80°~100° C. to convert the compound of the formula (VII) into the compound of the formula:

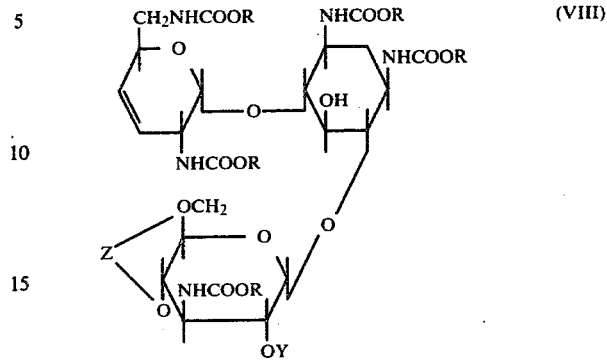

wherein R, Z and Y have the same meaning as defined above; and (5) treating the compound of the formula (VIII) thus obtained with an alkali or alkaline earth metal alcoholate, for example sodium methoxide, in a known manner to give 3',4'-dideoxy-3'-eno derivative of the formula (II) above.

The compound, penta-amino-protected, 4'',6''-hydroxyl-protected, 3',4'-β-epoxy derivative of kanamycin B represented by the formula:

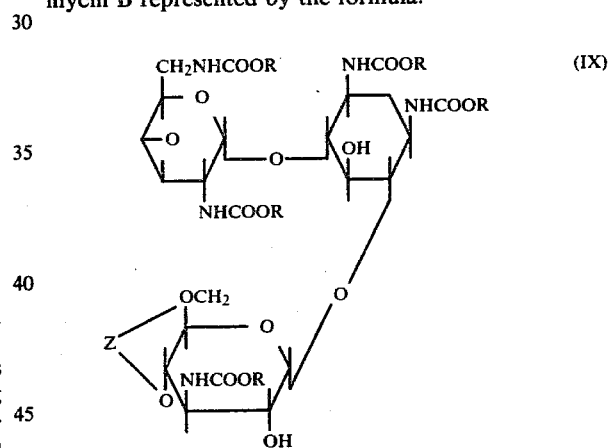

wherein R and Z have the same meaning as defined above which is to be used as starting compound of the first to third aspect processes according to this invention is a new compound and constitutes another aspect of this invention.

The new 3',4'-β-epoxy derivative of kanamycin B of the formula (IX) can be derived from kanamycin B through several reaction steps as explained below.

First of all, kanamycin B is subjected to amino-protecting step in a known manner. Thus, kanamycin B is reacted with a chloroformate of the formula RCOOCl wherein R represents a hydrogen atom or an alkyl or aryl group such as phenyl to protect all the five amino groups of kanamycin B in the form of urethane group —NHCOOR in the same manner as that described in Japanese Patent Publication No. 7595/75, affording penta-N-protected kanamycin B of the formula:

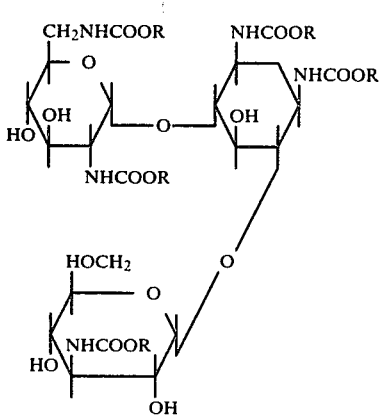
(X)

wherein R has the same meaning as defined above.

The next step is 4",6"-hydroxyl-protecting step which is also carried out in a known manner. Thus, the compound of the formula (X) may be reacted with a known hydroxyl-protecting agent selected from an alkylidenating agent, an arylidenating agent, a cyclohexylidenating agent and a tetrahydropyranylidenating agent. Typical examples of such hydroxyl-protecting agent include acetaldehyde, 2',2'-dimethoxypropane, anisaldehyde, benzaldehyde, dimethylacetal, tolualdehyde, 1,1-dimethoxycyclohexane and 1,1-dimethoxytetrahydropyran. The reaction may preferably be carried out in a polar organic solvent, e.g. dimethylformamide in the presence of a catalytic amount of p-toluene sulfonic acid at room temperatures, for example 15°~25° C. for 15~20 hours. This brings the selective introduction of the hydroxyl-protecting group in 4",6"-positions, thus yielding 4",6"-O-protected derivative of the formula:

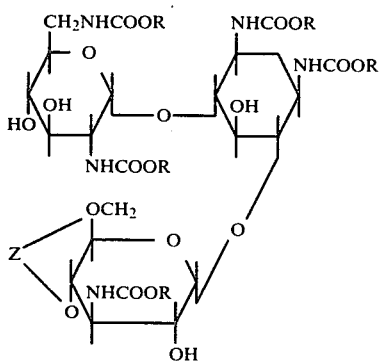
(XI)

wherein R has the same meaning as defined above and Z represents an alkylidene, arylidene, cyclohexylidene or tetrahydropyranylidene group. In this selective reaction, it is desired that the temperature should be kept not to exceed 30° C. because there may also occur the attack of the hydroxyl-protecting agent on the 3'- and 4'-hydroxyl groups at higher temperatures.

The compound of the formula (XI) is then subjected to acylation reaction for the purpose of selective protection of the 2"- and 3'-hydroxyl groups with hydroxyl-protecting group of an acyl type. The acylation step may usually be carried out by dissolving the compound of the formula (XI) in pyridine, adding an acylating agent such as an acyl chloride under a low temperature condition, preferably below 5° C. and maintaining the mixture under stirring for several hours.

Preferred acylating agent may be an acid chloride of an alkanoic acid having 2~4 carbon atoms such as acetyl chloride or an aroyl chloride such as benzoyl chloride. The use of benzoyl chloride is most preferred. The use of a temperature below 5° C. for the acylation step does not affect the 4'- and 5-hydroxyl groups which are relatively low in reactivity. Thus, 2",3'-diacyl derivative of the formula:

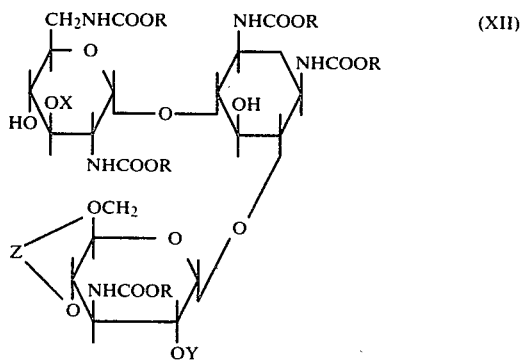
(XII)

wherein R and Z have the same meaning as defined above, and X and Y each represent an acyl group, for example an alkanoyl, particularly a lower alkanoyl such as acetyl or an aroyl such as benzoyl may be produced.

In the acylation step, 2"-monoacylated derivative, i.e. a compound of the formula (XII), but wherein X represents a hydrogen atom may be obtained, if desired for some purposes, by conducting the acylation reaction under a milder conditions. Thus, in case of benzoyl chloride being used as acylating agent, a major proportion of 2"-monobenzoyl derivative may be obtained under such conditions that benzoyl chloride is added at a temperature below 0° C. slowly and in small parts. On the other hand, at least a major proportion of 2",3'-dibenzoyl derivative may be obtained when benzoyl chloride is added at a time at a temperature between 0° C. and room temperatures, preferably 0° C. and 5° C. If 2"-monoacyl and 2",3'-diacyl derivatives are obtained in the form of a mixture, the isolation of the respective derivatives may be effected by a chromatographic separation technique in a known manner, per se, for example by silica-gel thin-layer chromatography using 2:1 by volume of chloroform-methanol as developer.

The compound of the formula (XII) is then subjected to 4'-O-sulfonylation to form 4'-O-sulfonylated derivative of the formula:

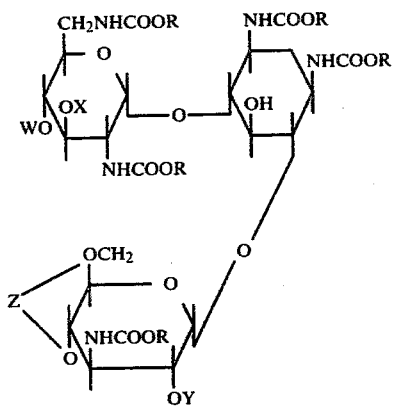

(XIII)

wherein R, Z, X and Y have the same meaning as defined above and W represents mesyl, tosyl or benzylsulfonyl group. This step may preferably be carried out by reacting the compound of the formula (XII) with mesyl chloride, tosyl chloride or benzylsulfonyl chloride in pyridine. The 4'-O-sulfonylation may be conducted at a temperature of up to 50° C. The most preferred sulfonylating agent is mesyl chloride.

The 4'-O-sulfonylated derivative of the formula (XIII) thus obtained is then converted to 3',4'-β-epoxy derivative of the formula (IX) above-mentioned as main product by treating it with a metal alcoholate. The epoxidation reaction may preferably be carried out by dissolving the compound of the formula (XIII) in a solvent, for example water, a lower alkanol such as methanol or ethanol, diglyme, sulforane, tetrahydrofuran or dimethylsulfoxide, adding to the solution a metal alcoholate, usually an alkali or alkaline earth metal alcoholate such as sodium, potassium, or lithium alcoholate, particularly a lower alkoxide, for example sodium methoxide or sodium ethoxide and maintaining the mixture at room temperatures, usually 15°~25° C., suitably for 1~3 hours. During the epoxidation reaction, the hydroxyl-protecting group Y in the 2"-position is removed because of alkaline condition, thus the free 2"-OH group is regenerated in the 3',4'-β-epoxidized derivative of the formula (IX).

3',4'-α-Epoxy derivative corresponding to the 3',4'-β-epoxy derivative of the formula (IX) may be derived from 3'-O-tosyl derivative corresponding to the 4'-O-sulfonylated derivative of the formula (XIII) above, i.e. the compound of the formula (XIII), but wherein W is hydrogen and X is tosyl group in the same manner as that of the 3',4'-epoxidation step as above-mentioned, i.e. by treating with an alkali-metal alcoholate such as sodium methoxide, details of which is given in DT-OS No. 2,555,479.

A diagramatic reaction scheme is given below to show the preparation of 3',4'-dideoxykanamycin B starting from kanamycin B via a new intermediate, 3',4'-β-epoxy derivative of the formula (IX), which is treated according to the processes of this invention.

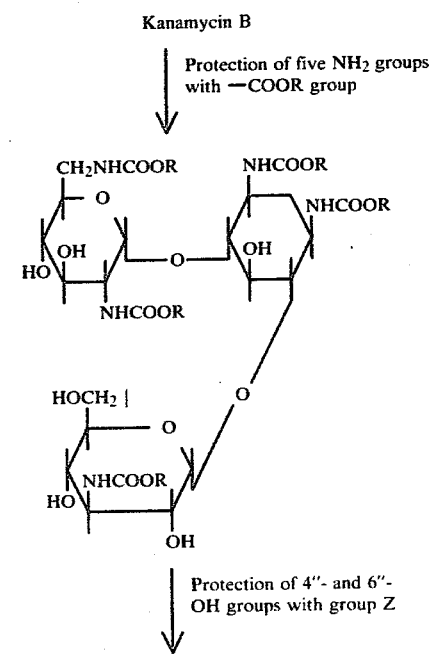

-continued
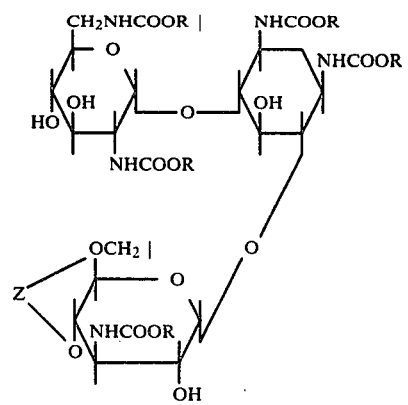
Protection of 2''- and 3'-
OH groups with acyl groups
Y and X, respectively
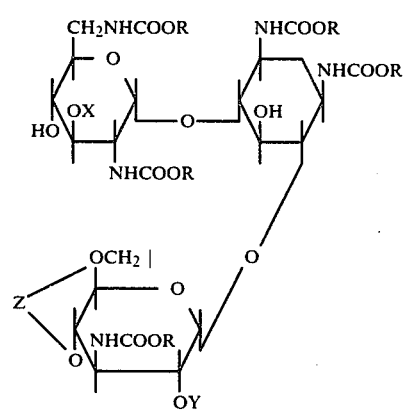
4'-O-Sulfonylation
(Introduction of W group)
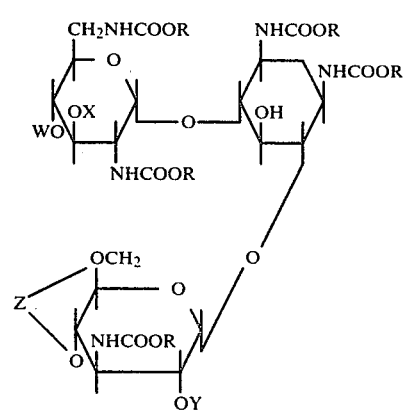
3',4'-Epoxidation with
an alcoholate -continued
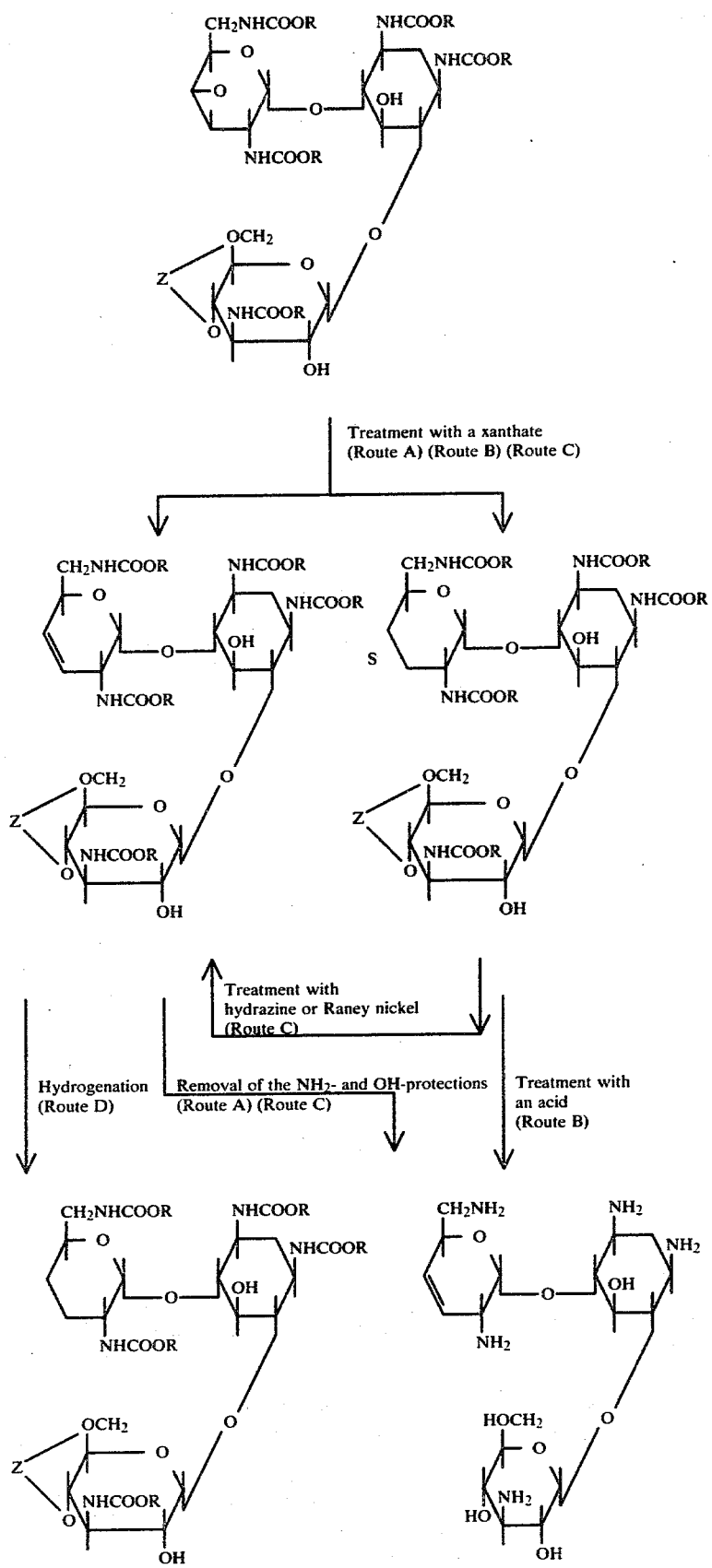

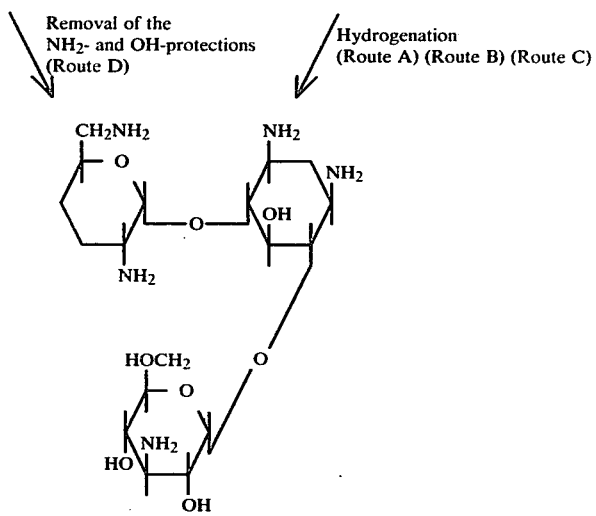

Removal of the NH₂- and OH-protections (Route D)

Hydrogenation (Route A) (Route B) (Route C)

Route A = The first aspect process of this invention
Route B = The second aspect process of this invention
Route C = The third aspect process of this invention
Route D = An alternative of the first or third aspect process of this invention

PREFERRED EMBODIMENTS OF THE INVENTION

This invention is further illustrated by way of Examples which include overall steps starting from kanamycin B and leading to the final product, 3',4'-dideoxykanamycin B, through several routes according to this invention.

EXAMPLE 1

(1) Preparation of penta-N-ethoxycarbonylkanamycin B

Penta-N-ethoxycarbonylkanamycin B was prepared from kanamycin B free base by the method described in Example 1 of British Pat. No. 1,349,302.

(2) Preparation of 2'',3'-di-O-benzoyl-penta-N-ethoxycarbonyl-4'',6''-O-cyclohexylidene-kanamycin B Penta-N-ethoxycarbonylkanamycin B (10 g) was suspended in dimethylformamide (70 ml), to which was added p-toluene sulfonic acid until the pH of the suspension was lowered below 3.0 and then added cyclohexanedimethylketal (10 ml). The mixture was maintained at 25° C. under stirring for 18 hours. The completion of the reaction was confirmed by thin layer chromatography using silica gel (made by Merck) as stationary phase and chloroform-methanol (10:1 by volume) as developer and the resulting reaction mixture was neutralized with triethylamine. The neutralized liquid was concentrated under vacuum to obtain a residual liquid of 25 ml which was then dissolved in pyridine (150 ml). After cooling the solution to a temperature of 0°~5° C., benzoyl chloride (3.9 ml) was added thereto and the mixture was kept to cause reaction for 3 hours. The completion of reaction was confirmed by thin layer chromatography. Water (5 ml) was added to the resulting mixture and the mixture was stirred at room temperature for 30 minutes, concentrated and poured into water (200 ml) to form precipitate which was recovered by filtration. Yield 12.7 g (95%). After the purification by a conventional silica-gel chromatography, the titled compound had the following physical properties: $[\alpha]_D^{25} + 76.6$ (c=1, pyridine); mp. 233°~235° C.

Elementary analysis:
Found: C 55.98; H 6.44; N 5.60%.
Calculated for $C_{53}H_{73}N_5O_{22}$: C 56.22; H 6.51; N 6.19%.

(3) Preparation of 2'',3'-di-O-benzoyl-penta-N-ethoxycarbonyl-4'',6''-O-cyclohexylidene-4'-O-mesylkanamycin B 2'',3'-di-O-benzoyl-penta-N-ethoxycarbonyl-4'',6''-O-cyclohexylidene-kanamycin B (5 g) was dissolved in pyridine (100 ml), to which was added mesyl chloride (1.4 ml) and the mixture was maintained at 40° C. under stirring for 1.5 hours. After the mixture was cooled to room temperature, water (5 ml) was added to the mixture to decompose the excess mesyl chloride and the mixture was concentrated. To the concentrate was added water (200 ml) to precipitate the titled compound, which was recovered by filtration. Yield 5.0 g (94%); $[\alpha]_D^{25} + 103.6°$ (c=1.0, pyridine); mp. 176°~179° C.

Elementary analysis:
Found: C 53.28; H 6.25; N 5.41; S 2.95%.
Calculated for $C_{54}H_{75}N_5O_{24}S$: C 53.59; H 6.25; N 5.79; S 2.65%.

(4) Preparation of 3',4'-β-epoxy-penta-N-ethoxycarbonyl-4'',6''-O-cyclohexylidene-kanamycin B 2'',3'-Di-O-benzoyl-penta-N-ethoxycarbonyl-4'',6''-O-cyclohexylidene-4'-mesyl-kanamycin B (5 g) was dissolved in methanol (100 ml), to which was added sodium methylate (2.2 g). The mixture was maintained at room temperature under stirring for 2 hours. After the completion of reaction was confirmed by thin layer chromatography using silica gel as stationary phase and carbon tetrachloride-acetone (1:1 by volume) as developer, the reaction mixture was ice-cooled, neutralized with concentrated hydrochloric acid (1.25 ml) and concentrated. To the neutralized concentrate was added water (100 ml) to precipitate the titled compound which was recovered by filtration. Yield 3.5 g (95%); $[\alpha]_D^{25}+37.8°$ (c=1.0, pyridine), mp. 254°~258° C. (decomposition with foaming).

Elementary analysis:
Found: C 51.86; H 6.89; N 7.58; O 33.67%.
Calculated for $C_{39}H_{63}N_5O_{19}$: C 51.69; H 7.02; N 7.73; O 33.55%.

(5) Preparation of 3',4'-dideoxy-3'-eno-penta-N-ethoxycarbonyl-4'',6''-O-cyclohexylidene-kanamycin B 3',4'-β-Epoxy-penta-N-ethoxycarbonyl-4'',6''-O-cyclohexylidene-kanamycin B (800 mg) was suspended in n-butanol (40 ml), to which was then added potassium n-butylxanthate (1.7 g) and the reaction was conducted at 80° C. for 4 hours. After the completion of reaction was confirmed by silica-gel thin layer chromatography using carbon tetrachloride-acetone (1:1 by volume) as developer, the mixture was cooled and washed with water (40 ml×2) and the resulting butanol layer was concentrated to dryness. Yield 900 mg. This was confirmed by silica-gel thin layer chromatography to be a mixture of 3',4'-dideoxy-3'-eno-penta-N-ethoxycarbonyl-4'',6''-cyclohexylidene-kanamycin B and 3',4'-episulfido-penta-N-ethoxycarbonyl-4'',6''-O-cyclohexylidene-kanamycin B in approximately 1:1 proportion.

The mixture was subjected to silica-gel thin layer chromatography using carbon tetrachloride-acetone (5:1 by volume) as developer, affording 3',4'-dideoxy-3'-eno-penta-N-ethoxycarbonyl-4'',6''-cyclohexylidene-kanamycin B with $[\alpha]_D^{26}$ of +24.7° (c=1.0, methanol) and 3',4'-episulfido-penta-N-ethoxycarbonyl-4'',6''-O-cyclohexylidene-kanamycin B with $[\alpha]_D^{25}$ of +10.8° (c=1.0, $H_2O$) and melting point of 250°~260° C. (with decomposition), separately.

Elementary analysis of the latter compound:
Found: C 50.41; H 6.95; N 7.45; S 3.48%.
Calculated for $C_{39}H_{63}N_5O_{18}S$: C 50.79; H 6.90; N 7.60; S 3.48%.

(6) Preparation of 3',4'-dideoxy-3'-eno-kanamycin B

3',4'-Dideoxy-3'-eno-penta-N-ethoxycarbonyl-4'',6''-O-cyclohexylidene-kanamycin B (475 mg) was dissolved in methanol (5 ml), to which was added an amount of 1 N HCl sufficient to adjust the pH value of the solution to 2.0. The solution was heated at 50° C. for 30 minutes and, after adding water (5 ml) and then barium hydroxide octahydrate (1.4 g), further heated to distill off the methanol and the remaining mixture was refluxed for 8 hours and then cooled.

Carbon dioxide gas was passed through the cooled mixture and barium carbonate thus formed was removed by filtration. Purification through a column of Amberlite CG-50 ($NH_4^+$ form) gave the titled compound. Yield 560 mg (26%).

Elementary analysis:
Found: C 47.85; H 7.95; N 15.40%.
Calculated for $C_{18}H_{35}N_5O_8$: C 48.11; H 7.80; N 15.59%.

(7) Preparation of 3',4'-dideoxykanamycin B

3',4'-Dideoxy-3'-eno-kanamycin B (120 mg) was dissolved in water (4 ml), to which Raney nickel (0.2 ml) was added. Hydrogen was passed through the solution for 2 hours under atmospheric conditions of temperature and pressure. After the catalyst used was filtered off, the filtrate was concentrated to dryness. Yield 108 mg (95%).

EXAMPLE 2

(1) Preparation of penta-N-t-butoxycarbonyl-kanamycin B

Kanamycin B (10 g) was added to a mixture of water (34 ml), triethylamine (24 ml) and dimethylformamide (48 ml). Then, t-butyl-S-(4,6-dimethylpyrimidin-2-yl)-thiol-carbonate (40 g) was added to the mixture at room temperature and the mixture was stirred at that temperature for 18 hours. Addition of water (150 ml) to the mixture formed crystals which were recovered by filtration and washed thoroughly with an aqueous saturated solution of ethyl acetate. Yield 20 g (100%). mp.229°~234° C. (decomposition with foaming).

Elementary analysis:
Found: C 52.61; H 7.86; N 6.93%.
Calculated for $C_{43}H_{77}N_5O_{20}$: C 52.47; H 7.90; N 7.12%.

(2) Preparation of 3',4'-β-epoxy-penta-N-t-butoxycarbonyl-4'',6''-O-cyclohexylidene-kanamycin B Penta-N-t-butoxykanamycin B (10 g) was treated in the same ways as those described in Example 1 (2), (3) and (4) above, yielding the titled compound. Yield 80%, $[\alpha]_D^{23}+27°$ C. (c=1.0; pyridine). mp. 232°~234° C. (decomposition with foaming).

(3) Preparation of 3',4'-episulfido-penta-N-t-butoxycarbonyl-4'',6''-O-cyclohexylidene-kanamycin B 3',4'-β-Epoxy-penta-N-t-butoxycarbonyl-4'',6''-O-cyclohexylidene-kanamycin B (10 g) was suspended in n-butanol (100 ml), to which was added potassium n-butylxanthate (9.5 g) and the reaction was conducted at 90° C. for 2 hours. After the reaction was completed, the mixture was cooled and washed twice with 100 ml portions of water and the butanol layer separated was concentrated to dryness, affording a mixture comprising 3',4'-episulfido-penta-N-t-butoxycarbonyl-4'',6''-cyclohexylidenekanamycin B and 3',4'-dideoxy-3'-eno-penta-N-t-butoxycarbonyl-4'',6''-cyclohexylidene kanamycin B. Yield 11 g. The crude product was subjected to silica gel chromatography using chloroform-methanol (50:1 by volume) as developer, to isolate 3',4'-episulfido-penta-N-t-butoxycarbonyl-4'',6''-cyclohexylidene-kanamycin B. Yield 3.9 g (35%). $[\alpha]_D^{25}+23°$ (c=1.0, pyridine). mp. 235°~238° C. (decomposition with foaming).

Elementary analysis:
Found: C 55.10; H 7.94; N 6.31; S 3.30%.
Calculated for $C_{49}H_{83}N_5O_{18}S$: C 55.39; H 7.89; N 6.59; S 3.02%.

(4) Preparation of 3',4'-dideoxy-3'-eno-kanamycin B

3',4'-Episulfido-penta-N-t-butoxycarbonyl-4'',6''-O-cyclohexylidene-kanamycin B (1.15 g) was dissolved in methanol (12 ml), to which was added concentrated hydrochloric acid (3 ml) and the reaction was conducted at room temperature for 3 hours.

The reaction mixture was concentrated to dryness and the resulting residue was dissolved in water (18 ml) and the pH of the solution was adjusted to 6.5 by the addition of 1 N sodium hydroxide solution (2.5 ml). The solution was passed through a column of 20 ml of Amberlite CG-50 (NH$_4^+$ form). The adsorbed column was washed with water and then 0.1 N aqueous ammonia and subsequently eluated with 0.3 N aqueous ammonia. The concentration of the eluate gave the titled compound. Yield 194 mg.

(5) Preparation of 3',4'-dideoxykanamycin B

3'4'-Dideoxy-3'-eno-kanamycin B (120 mg) was dissolved in water (4 ml), to which was added Raney nickel (0.2 ml) and hydrogen was passed through the mixture for 2 hours under atmospheric temperature and pressure conditions. After the catalyst was filtered off, the filtrate was concentrated to dryness, giving the tilted compound. Yield 108 mg (90%).

EXAMPLE 3

Preparation of 3',4'-episulfido-penta-N-ethoxycarbonyl-4",6"-O-cyclohexylidene-kanamycin B 3',4'-α-Epoxy-penta-N-ethoxycarbonyl-4",6"-O-cyclohexylidene-kanamycin B (100 mg) which was prepared by the method described in Example 1 of DT-OS 2,555,479 was dissolved in pyridine (5 ml), to which was added potassium ethyl xanthate (100 mg) and the mixture was refluxed for 1.5 hours and then concentrated to dryness. A mixture of water and chloroform (2:3 by volume) was added to the solid residue and the chloroform layer was separated, washed three times with 20 ml portions of water and concentrated to dryness, yielding 70 mg of a crude product comprising 3',4'-episulfido-penta-N-ethoxycarbonyl-4",6"-O-cyclohexylidene-kanamycin B and 3',4'-dideoxy-3-eno-penta-N-ethoxycarbonyl-4",6"-O-cyclohexylidene-kanamycin B.

The isolation of the respective compounds was carried out by thin layer chromatography in the same manner as that used in Example 1 (5) above.

EXAMPLE 4

(1) Preparation of 3',4'-dideoxy-3'-eno-penta-N-ethoxycarbonyl-4",6"-O-cyclohexylidene-kanamycin B 3',4'-Episulfido-penta-N-ethoxycarbonyl-4",6"-O-cyclohexylidene-kanamycin B (470 mg) which was prepared as described in Example 1 (5)(or Example 3(1)) above was dissolved in methanol (2 ml), to which was added hydrazine hydrate (0.22 ml) and the mixture was allowed to stand at room temperature for 2 hours. The reaction mixture was then concentrated to dryness and treated with water (20 ml) to form precipitate which was recovered by filtration. Yield 362 mg (80%). $[\alpha]_D^{26} +24.7°$ (c=1.0, methanol).

Elementary analysis:

Found: C 52.31; H 7.53; N 7.49%. Calculated for C$_{39}$H$_{65}$N$_5$O$_{18}$: C 52.50; H 7.36; N 7.85%.

(2) Preparation of 3',4'-dideoxy-3'-eno-kanamycin B

3',4'-Dideoxy-3'-eno-penta-N-Ethoxycarbonyl-4",6"-cyclohexylidene-kanamycin B (475 mg) was dissolved in methanol (5 ml) and treated in the same manner as that described in Example 1 (6), affording the titled compound.

(3) Preparation of 3',4'-dideoxykanamycin B

3',4'-Dideoxy-3'-eno-kanamycin B was treated as similar as in Example 1 (7), affording the titled compound.

EXAMPLE 5

(1) Preparation of 3',4'-dideoxy-3'-eno-penta-N-t-butoxy-4",6"-O-cyclohexylidene-kanamycin B 3',4'-Episulfido-penta-N-t-butoxycarbonyl-4",6"-O-cyclohexylidene-kanamycin B (585 mg) which was prepared as in Example 2 (3) was dissolved in methanol (7 ml), to which was added Raney nickel (R-100)(500 mg) and the mixture was stirred at room temperature (20° C.) for 2 hours. After the Raney nickel was removed by filtration, the filtrate was concentrated to dryness, affording the titled compound. Yield 450 mg (80%).

(2) Preparation of 3',4'-dideoxykanamycin B

3',4'-Dideoxy-3'-eno-penta-N-t-butoxy-4",6"-O-cyclohexylidene-kanamycin B (450 mg) was treated as similar as in Example 1 (6) and (7), affording the titled compound. Yield 90%.

EXAMPLE 6

(1) Preparation of 3',4'-β-epoxy-penta-N-t-butoxycarbonyl-4",6"-O-cyclohexylidene-2"-O-benzoyl-kanamycin B 3',4'-β-Epoxy-penta-N-t-butoxycarbonyl-4",6"-O-cyclohexylidene-kanamycin B (2.0 g) was dissolved in dry pyridine (40 ml), to which was added benzoyl chloride (0.8 ml) under ice-cooling and the mixture was allowed to stand for reaction at 5° C. for 30 minutes. Then, water (2 ml) was added to the reaction mixture and the mixture was concentrated to give a syrup which was then poured into water (20 ml) to form precipitate. The precipitate was recovered by filtration and dried to yield the titled compound. Yield 2.16 g (98.3%).

(2) Preparation of 4'-deoxy-4'-iodo-penta-N-t-butoxycarbonyl-4",6"-O-cyclohexylidene-2"-O-benzoyl-kanamycin B 3',4'-β-epoxy-penta-N-t-butoxycarbonyl-4",6"-O-cyclohexylidene-2"-O-benzoyl-kanamycin B (2.1 g) was dissolved in acetone (60 ml), to which were added sodium iodide (1.4 g), sodium acetate (80 mg) and glacial acetic acid (1.4 ml) and the resulting mixture was refluxed for about 8 hours.

After the completion of the reaction, the mixture was cooled to deposit crystals which were recovered by filtration. Yield 2.25 g (94%). mp. 171°~176° C. (with decomposition).

Elementary analysis:

Found: C 52.81; H 7.11; N 5.31; I 10.39%.

Calculated for C$_{43}$H$_{76}$N$_5$O$_{19}$I: C 52.62; H 6.94; N 5.48; I 9.93%.

(3) Preparation of 3',4'-dideoxy-3'-eno-penta-N-t-butoxycarbonyl-4",6"-O-cyclohexylidene-2"-O-benzoyl-kanamycin B 4'-Deoxy-4'-iodo-penta-N-t-butoxycarbonyl-4",6"-O-cyclohexylidene-2"-O-benzoyl-kanamycin B (452 mg) was dissolved in dry pyridine (9 ml), to which was added benzylsulfonyl chloride (305 mg) under cooling to 0°~5° C. for about 30 minutes.

After the completion of the reaction, methanol (0.18 ml) was added to the reaction mixture which was then heated to 90° C. for 50 minutes, cooled to room temperature. The mixture was concentrated to a syrup, to which water (10 ml) was added to deposit crystals. The crystals were recovered by filtration and washed with water to obtain the titled compound in the form of a wet cake.

Identification of the compound thus obtained was made by silica-gel thin layer chromatography using carbon tetrachloride-acetone (4:1 by volume) as developer.

(4) Preparation of 3',4'-dideoxy-3'-eno-penta-N-t-butoxycarbonyl-4",6"-O-cyclohexylidene-kanamycin B The wet cake of the compound obtained in the step (3) above was dissolved in methanol (20 ml), to which sodium methylate was added to adjust the pH to 9.0~10.0 and the mixture was stirred at room temperature for 30 minutes, neutralized with 1 N HCl and concentrated to a syrup. Addition of water to the syrup formed a precipitate which was recovered by filtration, washed with water and dried to afford the titled compound. Yield 360 mg (100%).

We claim:

1. Penta-amino-protected, 4",6"-hydroxyl-protected, 3',4'-episulfido derivatives of kanamycin B represented by the formula

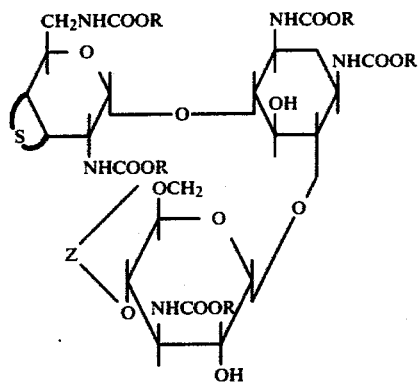

wherein R represents lower alkyl and Z represents lower alkylidene, arylidene formed from benzaldehyde, anisaldehyde or tolualdehyde, cyclohexylidene or tetrahydropyranylidene wherein the episulfido group is in the α- or β-position.

2. 3',4'-Episulfido-penta-N-ethoxycarbonyl-4",6"-O-cyclohexylidene-kanamycin B.

3. 3',4'-Episulfido-penta-N-t-butoxycarbonyl-4",6"-O-cyclohexylidene-kanamycin B.

* * * * *